United States Patent
Zhu et al.

(10) Patent No.: US 6,226,551 B1
(45) Date of Patent: May 1, 2001

(54) WIDE-BAND EVOKED RESPONSE SENSING FOR CAPTURE VERIFICATION

(75) Inventors: Qingsheng Zhu, Little Canada; Michael Lyden, Shoreview; Scot C. Boon, Lino Lakes, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/309,981

(22) Filed: May 11, 1999

(51) Int. Cl.[7] .......................................... A61N 1/37
(52) U.S. Cl. ................................................. 607/28
(58) Field of Search ........................... 607/27, 28

(56) References Cited

U.S. PATENT DOCUMENTS

| 5,161,529 | 11/1992 | Stotts et al. ......................... 128/419 |
| 5,222,493 | 6/1993 | Sholder ............................... 128/419 |
| 5,324,310 | 6/1994 | Greeninger et al. .................. 607/28 |
| 5,350,410 | 9/1994 | Kleks et al. ........................... 607/28 |
| 5,683,431 | 11/1997 | Wang .................................... 607/28 |
| 5,871,512 | 2/1999 | Hemming et al. .................... 607/28 |

Primary Examiner—Scott M. Getzow
(74) Attorney, Agent, or Firm—Nikolai, Mersereau & Dietz, P.A.

(57) ABSTRACT

A cardiac rhythm management device having a capture verification sensing circuit for use in either a normal beat to beat pacing mode or an autothreshold mode. The cardiac rhythm management device is coupled to one or more pacing leads having pacing/sensing electrodes coupled thereto, and includes a sensing circuit for sensing electrical activity of the patient's heart. The sensing circuit includes a sense amplifier electrically connected in a manner, wherein a polarity of an amplitude of the sensed signal corresponding to an evoked response is opposite a polarity of an amplitude of the sensed signal corresponding to afterpotential. The sensing circuit further includes a band pass filter having a single high pass pole.

9 Claims, 4 Drawing Sheets

WIDE-BAND EVOKED RESPONSE SENSING FOR CAPTURE VERIFICATION

BACKGROUND OF THE INVENTION

I. Field of the Invention

The present invention relates generally to the field of cardiac rhythm management devices, including atrial, ventricular, and dual chamber pacemakers. More specifically, the present invention relates to a portion of the sensing circuit of the cardiac rhythm management device that may be utilized during capture verification. The sensing circuit of the present invention includes a band pass filter having a single high pass pole and a sense amplifier electrically coupled within the cardiac rhythm management device. The sense amplifier is electrically coupled in a manner, wherein a polarity of an amplitude of a sensed signal corresponding to an evoked response is opposite a polarity of an amplitude of a sensed signal corresponding to afterpotential.

II. Discussion of the Prior Art

Regardless of the type of cardiac rhythm management device that is employed, all operate to stimulate excitable heart tissue cells adjacent to the electrode of the lead coupled to the rhythm management device. Response to myocardial stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is approximately equal to the concentration of potassium ions inside the cell membrane. However, the selective permeability also retains other negative particles within the cell membrane such that the inside of the cell membrane is negatively charged with respect to the outside when the cell is at rest.

When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibrils of the cell membrane. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation described above. The SA node comprises a bundle of unique cells disposed within the roof of the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles. The atrial depolarization from the SA node is detected by the atrioventicular (AV) node which, in turn, communicates the depolarization impulse into the ventricles via the Bundle of His and Purkinje fibers following a brief conduction delay.

In this fashion, ventricular systole lags behind atrial systole such that the blood from the ventricles is pumped through the body and lungs after being filled by the atria. Atrial and ventricular diastole follow wherein the myocardium is repolarized and the heart muscle relaxes in preparation for the next cardiac cycle. It is when this system fails or functions abnormally that a cardiac rhythm management device may be needed to deliver an electronic pacing stimulus to the heart so as to maintain proper heart rate and synchronization of the filling and contraction of the atrial and ventricular chambers of the heart.

The success of a cardiac rhythm management device in causing a depolarization or evoking a response hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture. This can be verified by lowering the stimulation energy level and monitoring for loss of capture at the new energy level.

The ability to detect capture in a cardiac rhythm management device is extremely desirable in that delivering stimulation pulses having energy far in excess of the patient's capture threshold is wasteful of the cardiac rhythm management device's limited power supply. In order to minimize current drain on the power supply, it is desirable to automatically adjust the cardiac rhythm management device such that the amount of stimulation energy delivered to the myocardium is maintained at the lowest level that will reliably capture the heart. To accomplish this, a process known as "capture verification" must be performed wherein the cardiac rhythm management device monitors to determine whether an evoked response or R-wave occurs in the heart following the delivery of each pacing stimulus pulse.

For the most part, prior art implantable cardiac rhythm management devices, including bradycardia and tachycardia pacemakers and cardiac defibrillators, have sense amplifier circuits for amplifying and filtering electrogram signals sensed through electrodes placed in or on the heart and which are coupled by suitable leads to the implantable cardiac rhythm management device. The signals emanating from the sense amplifier are applied to one input of a comparator circuit whose other input is connected to a reference potential. Only when an electrogram signal from the sense amplifier exceeds the reference potential threshold will it be treated as an evoked response. The source reference potential may be referred to as a sensing threshold. In some instances the amplitude of pacing artifact may be so great that it becomes difficult to distinguish the amplitude corresponding to an evoked response with the amplitude corresponding to artifact. Hence, there is a need for a capture verification circuit of a cardiac rhythm management device capable of differentiating between the amplitude corresponding to evoked response and the amplitude corresponding to artifact of a sensed signal. There is a further need for a capture verification circuit suitable for use with either unipolar or bipolar stimulation and which does not depend upon lead placement. These and numerous other disadvantages of the prior art necessitates the need for the method and apparatus provided by the present invention.

SUMMARY OF THE INVENTION

It is accordingly the objective of the present invention to provide for a cardiac rhythm management device having a capture verification sensing circuit which differentiates the amplitude of the stimulation artifact from the amplitude of the evoked response, without requiring unipolar sensing or low impedance leads. The capture verification sensing circuit of the present invention may be utilized with either unipolar or bipolar stimulation and is not restricted by location of the pacing/sensing electrodes. The cardiac rhythm management device may operate in a normal beat to beat pacing mode and/or an autocapture mode and may be electrically coupled to one or more known suitable leads having pacing/sensing electrodes coupled thereto.

Without limitation, the cardiac rhythm management device includes a power supply, controller coupled to receive sensed electrogram signals, and means controlled by the controller for both selectively delivering electrical stimuli to a patient's heart and for detecting at least one of intrinsic and generated stimulations, wherein the generated stimulation pulses are applied in response to control signals from the controller. The controller may be in any of several forms including a dedicated state device or a microprocessor with code, and may include ROM memory for storing programs to be executed by the controller and RAM memory for storing operands used in carrying out the computations by the controller. Those skilled in the art will appreciate that stimulation circuitry, sensing circuitry, timing circuitry, and wave detection circuitry among others may all be included within the controller. The controller and components contained therein or coupled thereto detect and distinguish cardiac depolarization deflections and noise deflections from the electrocardiogram signal. A peak detector, for example, may be utilized to determine the amplitudes of the cardiac depolarization deflections and artifact deflections. The capture verification circuit includes a dedicated evoked response sense amplifier that is utilized during a capture verification mode of the cardiac rhythm management device to reduce false capture declaration.

The capture verification circuit is formed as a part of the sensing circuit and includes the control means for controlling stimulation of a patient's heart and sensing means for sensing cardiac electrogram signals. The sensing means is electrically coupled to the controller and the electrodes, and includes a dedicated sense amplifier electrically connected to the electrodes and controller in a manner wherein a polarity of an amplitude of a sensed signal corresponding to an evoked response is opposite a polarity of an amplitude of the sensed signal corresponding to afterpotential. The sensing means also includes a band pass filter having a single high pass pole coupled between the electrodes and dedicated sense amplifier. Without limitation, the single high pass pole of the band pass filter has a frequency range of less than 10 Hz. The dedicated sense amplifier and band pass filter preserves the evoked response morphology and distinguishes the amplitude associated with artifact from the amplitude associated with evoked response.

OBJECTS

It is accordingly a principal object of the present invention to provide a capture verification sensing circuit suitable for use in unipolar or bipolar sensing, wherein the amplitudes associated with artifact and evoked response are distinguished.

Another object of the present invention is to provide a capture verification sensing circuit that reduces the loss of evoked response morphology during signal processing.

A further object of the present invention is to provide a capture verification sensing circuit suitable for use when stimulating either ventricle.

These and other objects and advantages of the present invention will be readily apparent to those skilled in the art from a review of the following detailed description of the preferred embodiment in conjunction with the accompanying claims and drawings in which like numerals in the several views refer to corresponding parts.

DESCRIPTION OF THE PREFERRED EMBODIMENT

The present invention represents broadly applicable improvements to an implantable cardiac rhythm management device capable of automatically verifying capture or evoked response of a patient's heart. The cardiac rhythm management device includes a sensing circuit that distinguishes the evoked response from the artifact of a detected signal. The embodiments of the sensing circuit detailed herein are intended to be taken as representative or exemplary of those in which the improvements of the invention may be incorporated and are not intended to be limiting.

Figure 1:
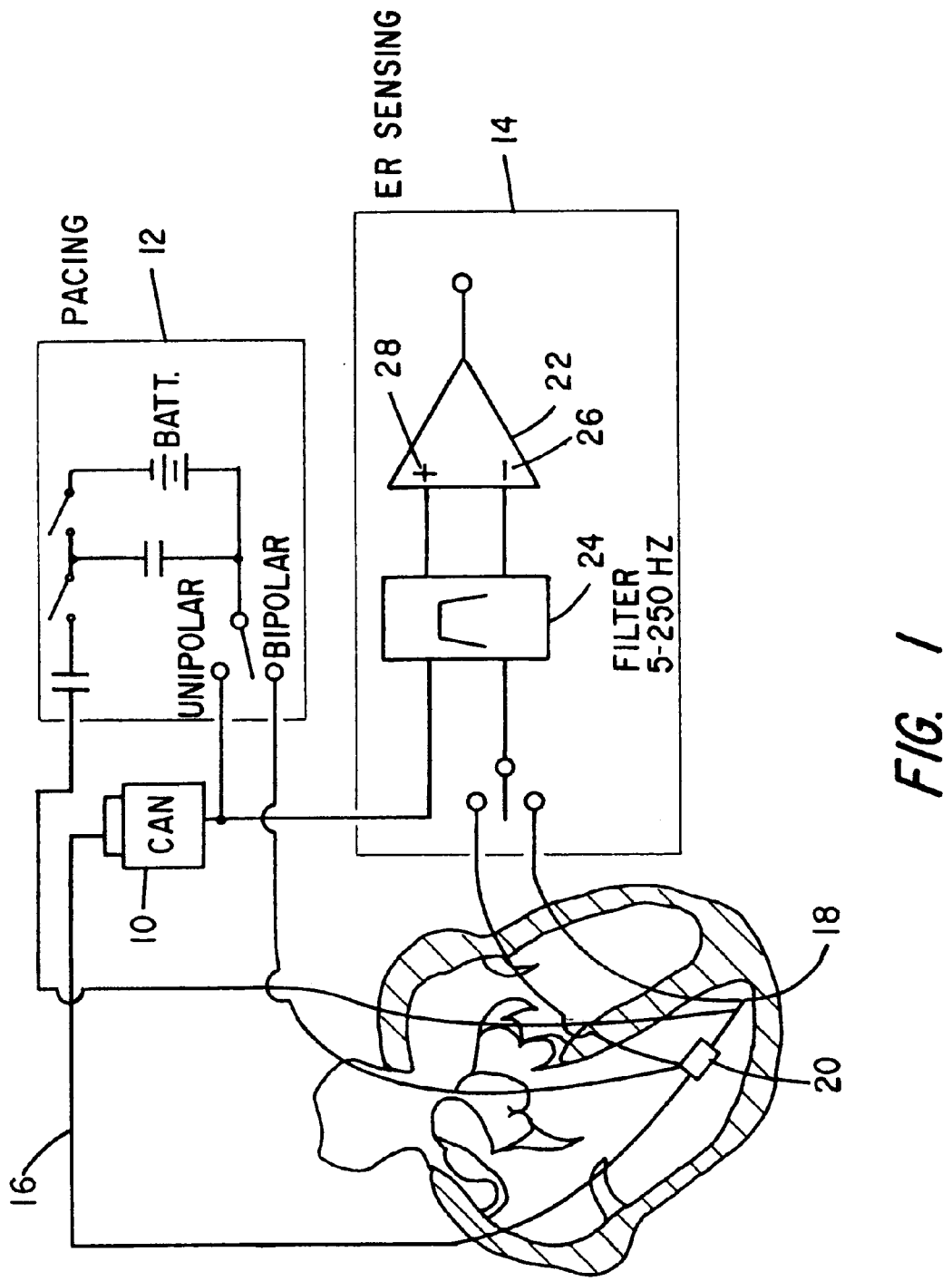
FIG. 1 is a partial sectional view of a lead positioned within the ventricle of a heart and shown electrically coupled to the pacing and sensing circuits, wherein the pacing and evoked response sensing circuits are shown partially in block form and exploded from the housing or can of the cardiac rhythm management device.

Referring first to FIG. 1, for purposes of illustration and ease of discussion, the present invention will be described in connection with an implantable cardiac pacer having an external housing or can 10, wherein a power supply and controller are contained therein. The pacer includes a pacing circuit and evoked response sensing circuit, a portion of each of which is shown enclosed by blocks 12 and 14 respectively. As described above, the controller may be in any of several forms including a dedicated state device or a microprocessor with code, and may include ROM memory for storing programs to be executed by the controller and RAM memory for storing operands used in carrying out the computations by the controller. The controller may include a pulse generator and pacing circuit 12 for selectively delivering electrical stimuli to a patient's heart and an evoked response sensing circuit 14 for detecting paced stimulations of the patients heart. One or more leads of known suitable construction may be electrically connected to the cardiac pacer. The lead 16 couple to the can 10 includes electrodes 18 and 20 positioned in the right ventricle for pacing and sensing therein. The electrodes 18 and 20 are electrically coupled to the cardiac pacer and the pacing and sensing circuits 12 and 14 contained therein. The evoked response sensing circuit 14 includes a dedicated sense amplifier 22 and single high pass pole band pass filter 24. The negative terminal or pole of the sense amp 22 is connected via a switch 26 to either electrode 18 or 20. The positive terminal or pole of the sense amplifier 22 is electrically coupled to the electrically conductive housing 10 or indifferent electrode of the cardiac rhythm management device. In this manner, as will be described in greater detail below, the polarity of the amplitude associated with artifact is opposite the polarity of the amplitude associated with evoked response.

Figure 2:
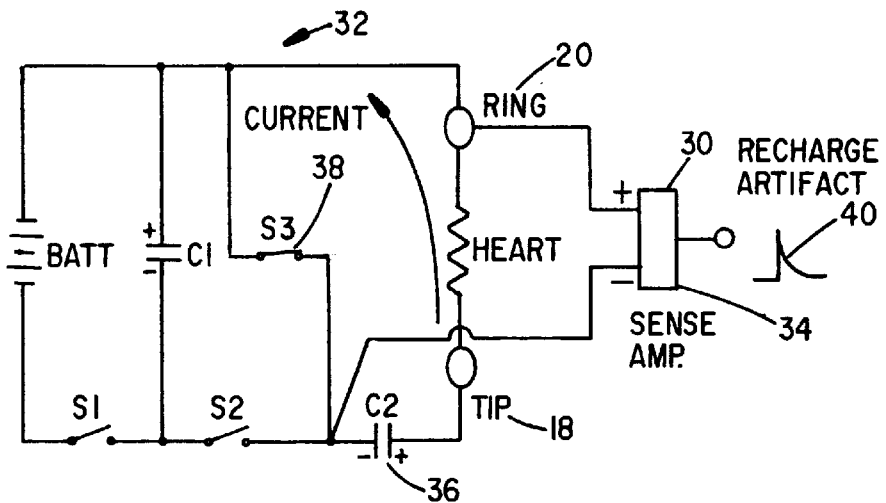
FIG. 2 is a partial schematic of a conventional evoked response sensing circuit showing the direction of flow of the signal and resulting polarity of the amplitude of the signal associated with artifact.
Figure 3:
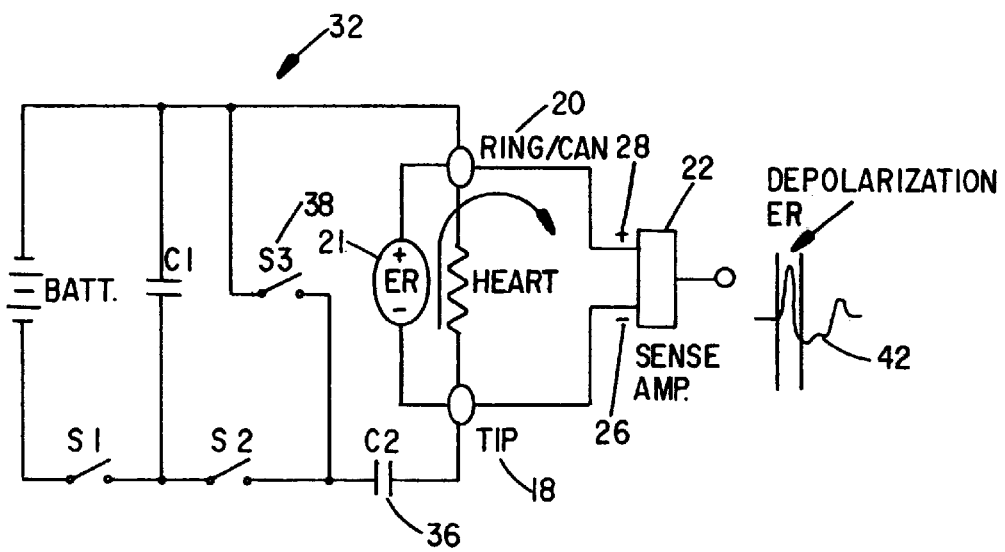
FIG. 3 is a partial schematic of the dedicated sense amplifier of the present invention showing the direction of flow of the signal and resulting polarity of the amplitude of the signal associated with the evoked response.
Figure 4:
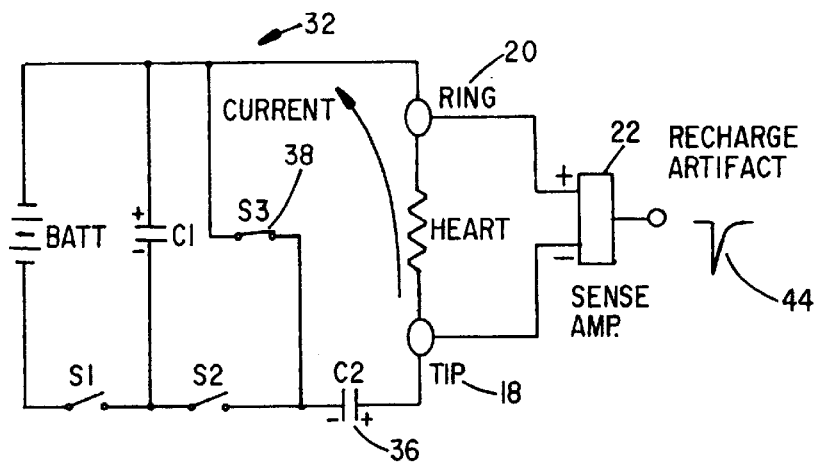
FIG. 4 is a partial schematic of the dedicated sense amplifier of the present invention showing the direction of flow of the signal and resulting polarity of the amplitude of the signal associated with artifact.

Referring to FIGS. 2–4 the current flow of the evoked response and recharge artifact are shown. FIG. 2 shows a typical sense amplifier 30 electrically coupled to a pacing circuit 32. The negative terminal 34 of the sense amplifier 30 is electrically coupled after the coupling capacitor 36, wherein when switch 38 is closed to start recharge, artifact signals 40 observed due to recharge result in an amplitude having a positive polarity. FIG. 3 shows a dedicated sense amplifier 22 electrically coupled to the pacing circuit 32. The negative terminal 26 of the amplifier 22 is electrically coupled before the coupling capacitor 36. In this manner when a pace pulse captures the heart, the extracellular current flows towards the tip electrode 18 where the activation originated and the evoked response polarity is indicated at 21. The depolarization signal 42 presents to the sense amplifier 30 with the current flow direction reverse to the recharge signal. Thus, a positive polarity of the amplitude associated with evoked response is observed. FIG. 4 shows the sense amplifier 30 capacitively coupled before the coupling capacitor 36. When switch 38 closes, the signals 44 observed due to recharge result in an amplitude having a negative polarity.

Figure 5:
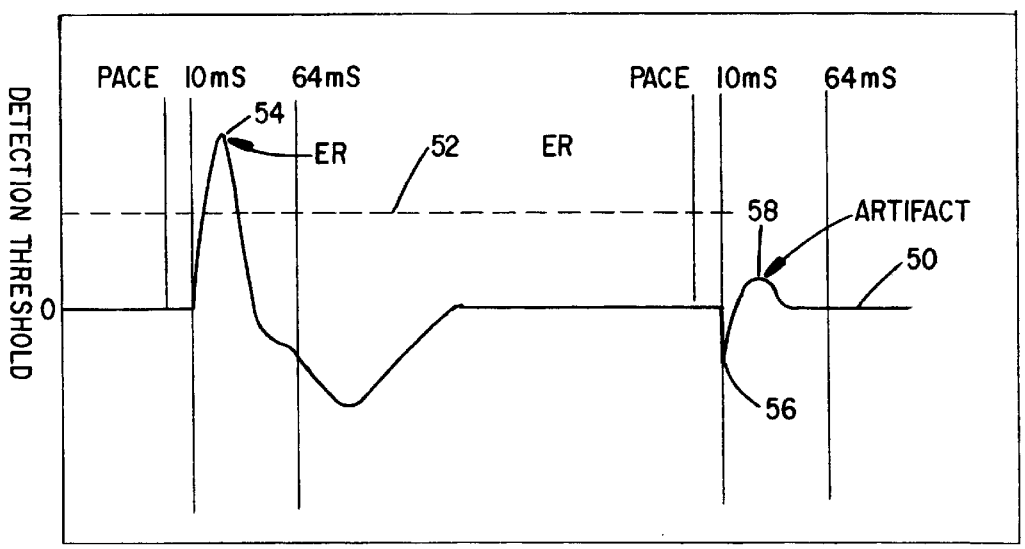
FIG. 5 is a graph of an electrocardiogram signal over time sensed with the sensing circuit of the present invention.

Referring now to FIG. 5 an electrocardiogram signal is shown resulting from a pacing stimulus. Without limitation, the dedicated evoked response sense amplifier is duty cycled and is only turned on by the controller during a predefined capture detection window. The capture detection window shown in FIG. 5 is defined by the time from pacing to 64 msec after pace. Those skilled in the art will appreciate that the capture detection window may be defined either longer or shorter than the period shown in FIG. 5. The evoked response detection threshold is shown by dotted line 52, wherein a positive peak amplitude associated with the evoked response exceeds the evoked response detection threshold. Later in time, the artifact associated with recharge is seen having primarily a negative peak amplitude. The minor portion 58 of the signal associated with artifact 56 does not exceed the evoked response detection threshold and does not result in false capture declaration.

Figure 6:
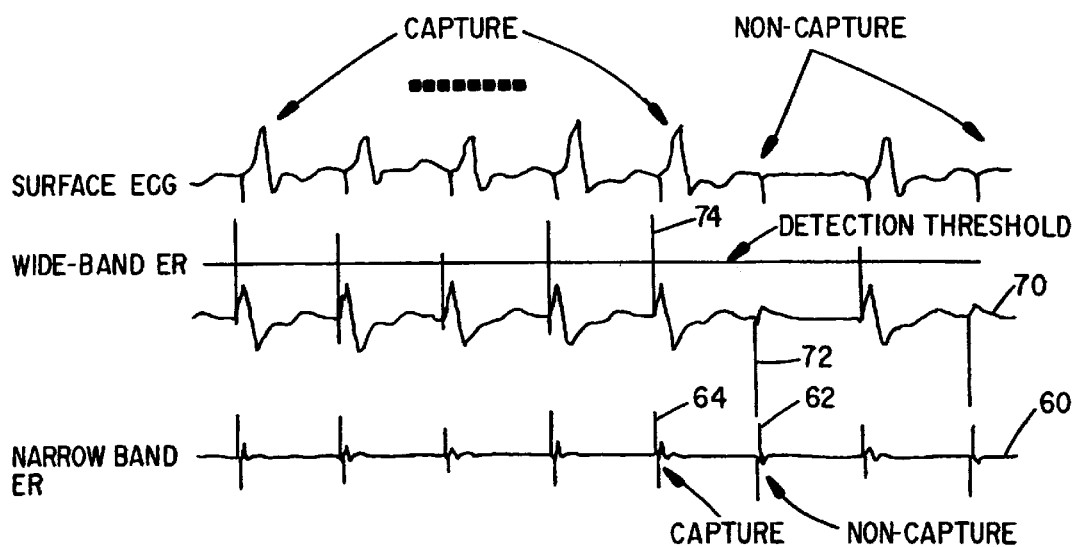
FIG. 6 is a graph of a surface electrocardiogram signal, an electrocardiogram signal processed with a single high pass pole band pass filter and an electrocardiogram signal processed with a band pass filter having multiple high pass poles observed over the same period of time.

FIG. 6 further shows the advantage of utilizing a single high pass pole band pass filter in conjunction with a dedicated evoked response sense amplifier. A typical signal processed through a narrow-band filter (10–100 Hz) results in a signal 60 having amplitudes associated with evoked response and/or artifact that are difficult to distinguish. For example, the portion of the narrow-band signal identified as non-capture 62 has a positive polarity that is nearly as large as the prior positive polarity of the portion 64 corresponding to capture. Thus, it is difficult to distinguish the evoked response and artifact of a signal processed through a narrow-band filter. In contrast, the same detected signal processed through a single high pass pole band pass filter results in a signal 70, wherein a portion of the signal 72 associated with artifact has an amplitude having a negative polarity, whereas a portion of the signal 74 associated with evoked response has an amplitude having a positive polarity. Thus, the capture verification circuit of the present invention having a dedicated evoked response sense amplifier electrically coupled in a manner wherein a polarity of an amplitude of a sensed signal corresponding to an evoked response is opposite a polarity of an amplitude of the sensed signal corresponding to afterpotential is particularly useful in verifying capture.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself

What is claimed is:

1. A capture verification circuit in a cardiac rhythm management device for use in at least one of a normal mode and autothreshold mode, said capture verification circuit including:
   (a) control means for controlling stimulation of a patient's heart;
   (b) electrodes positioned within the heart and electrically connected to said control means; and
   (c) sensing means for sensing cardiac electrogram signals electrically coupled to said control means and said electrodes, said sensing means having a sense amplifier electrically connected to said electrodes and said control means in a manner wherein a polarity of an amplitude of a sensed signal corresponding to an evoked response is opposite a polarity of an amplitude of the sensed signal corresponding to afterpotential wherein said sensing means includes a single high pass pole band pass filter.

2. The capture verification circuit as recited in claim 1, further including a single high pass pole band pass filter coupled between said electrodes and said sense amplifier.

3. The capture verification circuit as recited in claim 2, wherein said single high pass pole has a frequency range of less than 10 Hz.

4. The capture verification circuit as recited in claim 1, wherein a positive pole of the sense amplifier is coupled to an indifferent contact of the cardiac rhythm management device and a negative pole of the sense amplifier is coupled to said electrodes.

5. The capture verification circuit as recited in claim 1, wherein said sensing means includes a dedicated evoked response sense amplifier.

6. A capture verification circuit in a cardiac rhythm management device for use in at least one of a normal mode and autothreshold mode, said capture verification circuit including:

(a) control means for controlling stimulation of a patient's heart;

(b) electrodes positioned within the heart and electrically connected to said control means; and (c) sensing means for sensing cardiac electrogram signals, said sensing means being electrically coupled to said control means and said electrodes, and having a sense amplifier electrically connected to said electrodes and said control means in a manner wherein a polarity of an amplitude of a sensed signal corresponding to an evoked response is opposite a polarity of an amplitude of the sensed signal corresponding to afterpotential, said sense amplifier includes a band pass filter having a single high pass pole.

7. The capture verification circuit as recited in claim 6, wherein said single high pass pole has a frequency range of at less than 10 Hz.

8. The capture verification circuit as recited in claim 6, wherein a positive pole of the sense amplifier is coupled to an indifferent contact of the cardiac rhythm management device and a negative pole of the sense amplifier is coupled to said electrodes.

9. The capture verification circuit as recited in claim 6, wherein said sensing means includes a dedicated evoked response sense amplifier.

* * * * *